(12) United States Patent
Schuette et al.

(10) Patent No.: US 11,813,800 B2
(45) Date of Patent: Nov. 14, 2023

(54) METHOD AND APPARATUS FOR IMPROVED ULTRASONIC BONDING

(71) Applicant: Curt G. Joa, Inc., Sheboygan Falls, WI (US)

(72) Inventors: David E. Schuette, Sheboygan, WI (US); Jeffrey W. Fritz, Plymouth, WI (US); Justin M. Lafferty, Marshfield, WI (US)

(73) Assignee: CURT G. JOA, INC., Sheboygan Falls, WI (US)

( * ) Notice: Subject to any disclaimer, the term of this patent is extended or adjusted under 35 U.S.C. 154(b) by 0 days.

(21) Appl. No.: 17/457,715

(22) Filed: Dec. 6, 2021

(65) Prior Publication Data

US 2022/0088885 A1 Mar. 24, 2022

Related U.S. Application Data

(63) Continuation of application No. 16/508,422, filed on Jul. 11, 2019, now Pat. No. 11,192,310.

(51) Int. Cl.
*B29C 65/08* (2006.01)
*B29C 65/00* (2006.01)

(52) U.S. Cl.
CPC ............. *B29C 65/08* (2013.01); *B29C 66/90* (2013.01); *B29C 66/81463* (2013.01)

(58) Field of Classification Search
CPC ... B29C 65/08; B29C 66/90; B29C 66/81463; B29C 66/93411; B29C 65/083; B29C 65/085; B29C 65/086; B29C 65/087; B29C 65/088; B29C 65/645; B29C 66/93451
See application file for complete search history.

(56) References Cited

U.S. PATENT DOCUMENTS

| 7,449,084 B2 | 11/2008 | Nakakado |
| 8,776,856 B2 | 7/2014 | Yamamoto |
| 9,186,845 B2 | 11/2015 | Shimada |
| 10,537,479 B2 | 1/2020 | Schuette et al. |

(Continued)

FOREIGN PATENT DOCUMENTS

| JP | 2012120775 A | 6/2012 |
| JP | 2013199090 A | 10/2013 |

(Continued)

*Primary Examiner* — George R Koch
(74) *Attorney, Agent, or Firm* — KLINTWORTH & ROZENBLAT IP LLP

(57) ABSTRACT

A system and method for controlling the speed of both a continuous web and a bonding apparatus is provided in order to effectuate stronger bonds in the web. The bonding system includes a velocity changing device for increasing and decreasing a velocity of the web in a machine direction, an anvil and a corresponding ultrasonic horn that interact to form ultrasonic bonds on the web, and an anvil actuator configured to control a movement of the anvil. A control system is also included in the bonding system for controlling operation of the anvil actuator the velocity changing device, with the control system programmed to decrease a moving velocity of the web from a feed velocity to a bonding velocity as the web passes between the anvil and the ultrasonic horn and control movement of the anvil to synchronize the movement of the anvil with the moving velocity of the web.

20 Claims, 13 Drawing Sheets

(56) References Cited

U.S. PATENT DOCUMENTS

2004/0030432 A1* 2/2004 Popp .................. B65H 23/1886
700/109
2015/0298390 A1* 10/2015 Shimada ............... B29C 66/431
156/580.2

FOREIGN PATENT DOCUMENTS

| JP | 2014028492 A | 2/2014 |
| JP | 2014144210 A | 8/2014 |
| JP | 2018015961 A | 2/2018 |

* cited by examiner

METHOD AND APPARATUS FOR IMPROVED ULTRASONIC BONDING

CROSS-REFERENCE TO RELATED APPLICATION

The present application is a continuation of, and claims priority to, U.S. patent application Ser. No. 16/508,422, filed Jul. 11, 2019, now issued as U.S. Pat. No. 11,192,310 B2, the disclosure of which is incorporated herein by reference in its entirety.

BACKGROUND OF THE INVENTION

Embodiments of the invention relate generally to disposable hygiene products and more specifically, to methods and apparatuses for processing disposable hygiene products such as baby diapers, adult diapers, disposable undergarments, incontinence devices, sanitary napkins and the like. More specifically, the invention relates to controlling and positioning webs or web segments of a disposable diaper and bonding them, with an apparatus and method being provided for performing bonding on at least one continuously moving web using a bonding apparatus, where the speeds of the web and the bonding apparatus may be synchronized to effectuate stronger bonds in the web. Various types of automatic manufacturing equipment have been developed which produce the desired results with a variety of materials and configurations.

The invention disclosed herein relates to a method for controlling pieces traveling on a production line, specifically a bonding system for bonding a plurality of webs together. Although the description provided relates to diaper manufacturing, the method is easily adaptable to other applications. Although the description provided relates to bonding portions of diapers, the method is easily adaptable to other products, other disposable products, other diaper types and other portions of diapers.

In the manufacture of disposable hygiene products, such as diapers, it is known to bond different layers of material, such as two layers of continuously moving substrate web materials, by constrictively passing the webs through a bonding apparatus such as an ultrasonic welding system. The ultrasonic welding system includes an ultrasonic horn and an anvil roll separated by a gap therebetween through which the web materials are constrictively passed, with it being recognized that the welding system may be a rotary ultrasonic welding system or a blade ultrasonic welding system. Typically, the anvil roll includes one or more arrays of raised projections configured to bond the webs in a predetermined bond pattern, with the ultrasonic horn being capable of expressing ultrasonic energy at a bonding surface to ultrasonically bond the webs as the webs travel between the ultrasonic horn and the anvil roll. The rotary anvil and the ultrasonic horn cooperate with each other to ultrasonically bond the web layers to one another. During the bonding process, the web layers are exposed to an ultrasonic emission from the horn that increases the vibration of the particles in the web layers. The ultrasonic emission or energy is concentrated at specific bond points where frictional heat fuses the web layers together without the need for consumable adhesives.

It is recognized that the consistency and quality of the ultrasonic bonds is dependent on the consistency of the force exerted on the webs by the combination of the anvil roll and the bonding roll; the time during which the web is being pressed in the constrictive nip (i.e., dwell time) which is dependent on, among other things, the operating speed; and the types of materials being bonded. The consistency and quality of the bonds are also dependent on the frequency and amplitude of the vibrations of the ultrasonic horn. Among these variables, the dwell time is a primary factor that should be properly controlled in order to form bonds of sufficient quality. While typically the speed of the web is controlled in order to increase the dwell time when forming the bonds, it is recognized that controlling of the web speed alone may not be adequate to form bonds of desired quality.

Accordingly, there is a need for an improved apparatus and method for performing bonding on at least one continuously moving web using a bonding apparatus.

BRIEF DESCRIPTION OF THE INVENTION

In accordance with one aspect of the invention, a system for bonding a web comprising at least a pair of web layers includes a velocity changing device for increasing and decreasing a velocity of the web in a machine direction, an anvil and a corresponding ultrasonic horn that interact to form ultrasonic bonds on the web, and an anvil actuator configured to control a movement of the anvil. A control system is also included in the bonding system for controlling operation of the anvil actuator the velocity changing device, with the control system programmed to decrease a moving velocity of the web from a feed velocity to a bonding velocity as the web passes between the anvil and the ultrasonic horn and control movement of the anvil to synchronize the movement of the anvil with the moving velocity of the web.

In accordance with another aspect of the invention, a method for bonding a web having at least a pair of web layers includes moving a web in a machine direction via a feeding assembly, the feeding assembly configured to selectively control a velocity of the web. The method also includes feeding the web to one or more bonding apparatuses, each of the one or more bonding apparatuses comprising an anvil, an ultrasonic horn that interacts with the anvil to form ultrasonic bonds on the web, and an anvil actuator configured to control a velocity of the anvil. The method further includes controlling operation of the anvil actuator and the feeding assembly to synchronize the velocity of the web with a velocity of the anvil by decreasing the velocity of the web and the velocity of the anvil to a web bonding velocity and an anvil bonding velocity as the web passes between the anvil and the ultrasonic horn.

These and other advantages and features will be more readily understood from the following detailed description of preferred embodiments of the invention that is provided in connection with the accompanying drawings.

BRIEF DESCRIPTION OF THE DRAWINGS

The drawings illustrate embodiments presently contemplated for carrying out the invention.

In the drawings.

DETAILED DESCRIPTION

Embodiments of the invention provide for a method and apparatus for controlling the speed of both a continuous web and a bonding apparatus in order to effectuate stronger bonds in the web, including phasing and/or synchronization of these speeds at a desired bonding time. Embodiments of the invention also provide for a method and apparatus for selectively controlling the distance between a selected anvil-horn combination and one or more adjacent anvil-horn combinations.

Figure 1:
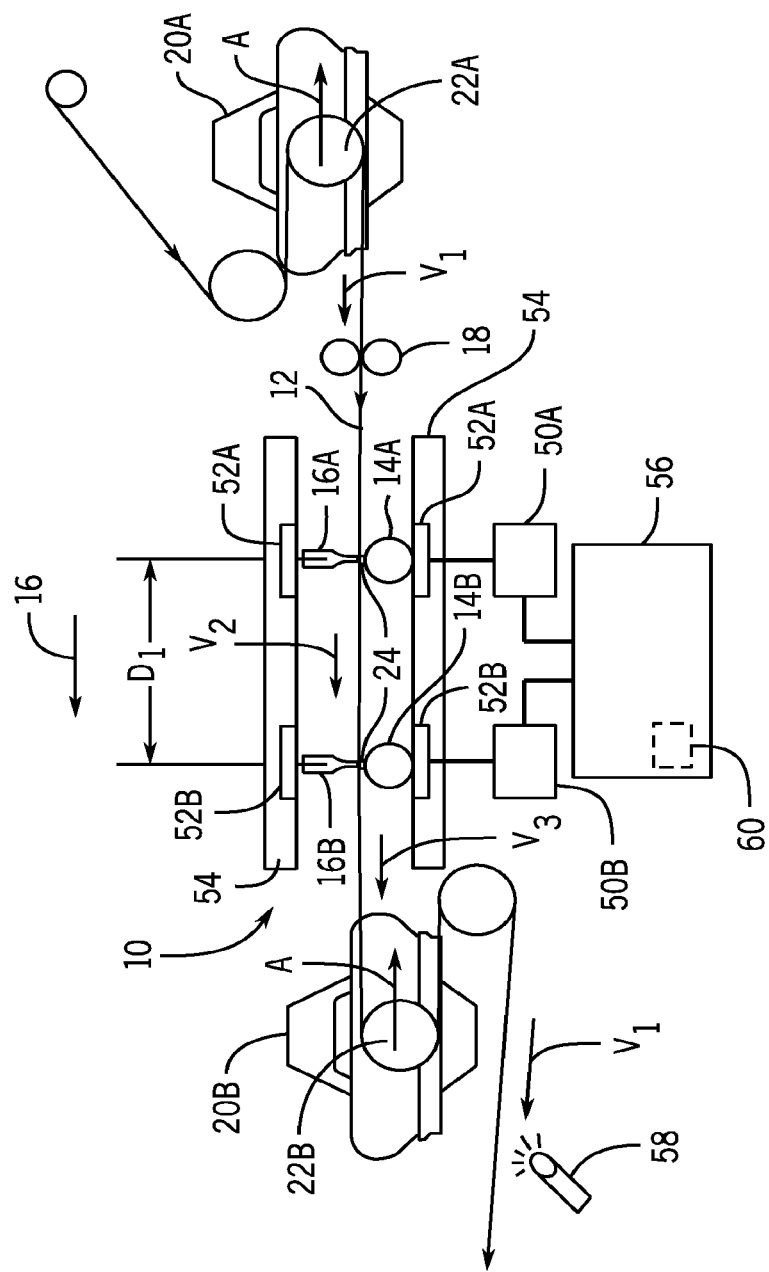
FIG. 1 is a schematic view of a bonding system including a plurality of anvil-horn combinations, according to an embodiment of the invention.
Figure 2:
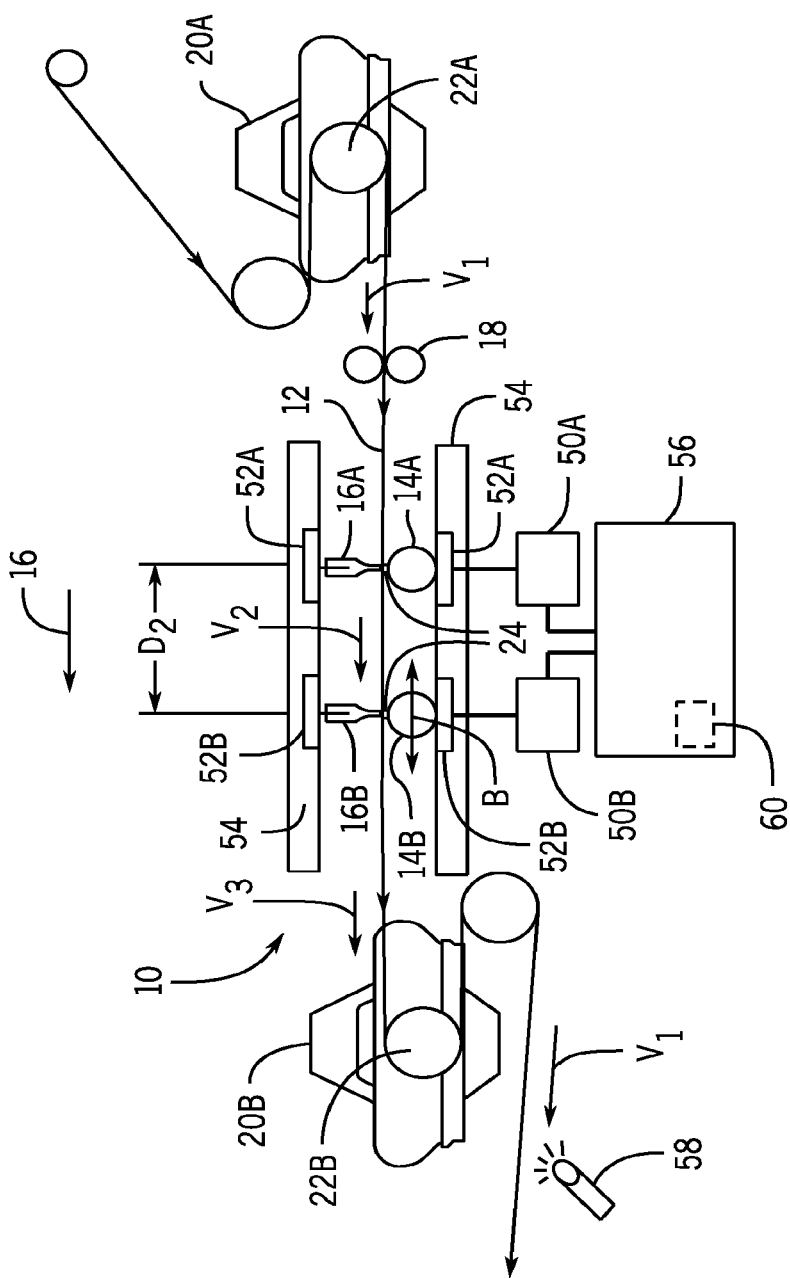
FIG. 2 is a schematic view of the bonding system of FIG. 1 with one or more of the anvil-horn combinations moved to vary a distance between the anvil-horn combinations.
Figure 3:
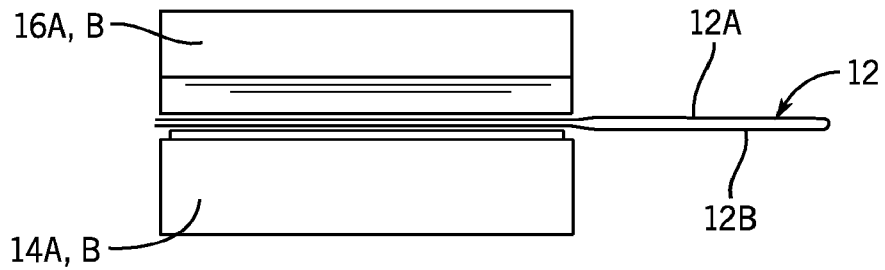
FIG. 3 is a cross sectional view of an anvil and horn of the bonding system of FIG. 1, showing the passage of web layers to be bonded therebetween.
Figure 4A:
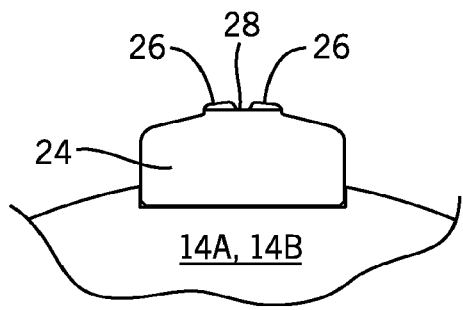
FIG. 4A is an enlarged view of an anvil insert for use with the anvils of the bonding system of FIG. 1, according to an embodiment of the invention.
Figure 4B:
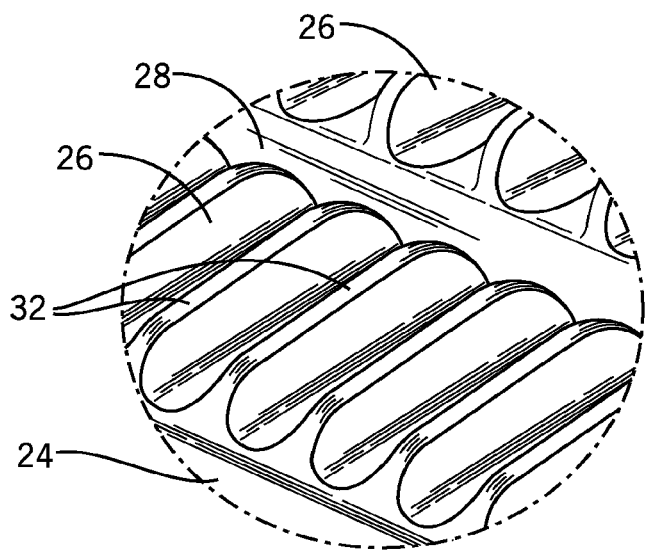
FIG. 4B is an enlarged perspective view of the anvil insert illustrated in FIG. 4A.

Referring first to FIGS. 1 and 2, a bonding system 10 is disclosed according to an embodiment of the invention that is configured to bond a web of material 12—with the web 12 formed from a first web layer 12A and a second web layer 12B (as described hereafter) or from a unitary web structure that is folded. The system 10 includes a first anvil 14A, a second anvil 14B, a first ultrasonic horn 16A, and a second ultrasonic horn 16B. The first and second anvils 14A, 14B are laterally spaced apart inline and in a machine direction 16 by a predetermined distance d1. The system 10 also includes carrying means 18 for carrying the webs 12 so that the webs 12 pass a first gap between the first anvil 14A and the first ultrasonic horn 16A and then a second gap between the second anvil 14B and the second ultrasonic horn 16B. The first and second ultrasonic horns 16A, 16B apply vibration energy to the web 12 simultaneously and function in cooperation with a respective anvil 14A, 14B to bond a respective portion of the web 12, as shown in FIG. 3 for example.

System 10 further includes a velocity-changing device for increasing and decreasing the moving velocity of the web 12. In the illustrated embodiment velocity-changing device includes a first web festoon accumulator 20A having a first accumulator roller 22A, and a second web festoon accumulator 20B having a second accumulator roller 22B. The first web festoon accumulator 20A receives the webs 12 flowing from an upstream side and releases the webs toward the ultrasonic horns 16A, 16B while the second web festoon accumulator 20B receives the webs 12 from the ultrasonic horns 16A, 16B and moves the webs 12 toward a downstream side. The velocity-changing device further includes means for moving the first and second accumulator rollers 22A, 22B in a unison, linear manner to thereby change the velocity V1 of the web 12 received. When the first and second accumulator rollers 22A, 22B move in the direction of arrow A, the velocity V1 of the web 12 from the upstream side is moved to second, slower velocity V2, such that the dwell time of the web 12 during the bonding operation is adequate for proper bonding. The anvil rolls 14A, 14B are preferably synchronized such that the system 10 will produce two bonds simultaneously during the slower V2 velocity. Once the web 12 is bonded, the accumulator rollers 22A, 22B move in the direction opposite arrow A and the webs 12 move at velocity V3 to be ultimately transported by the second web festoon accumulator 20B at the first V1 velocity and in a downstream direction. In alternative embodiments, the velocity-changing device may be a vertical accumulator series or horizontal accumulator series, either of which may include any number of roll assemblies to selectively control the velocity of the web 12.

Figure 5A:
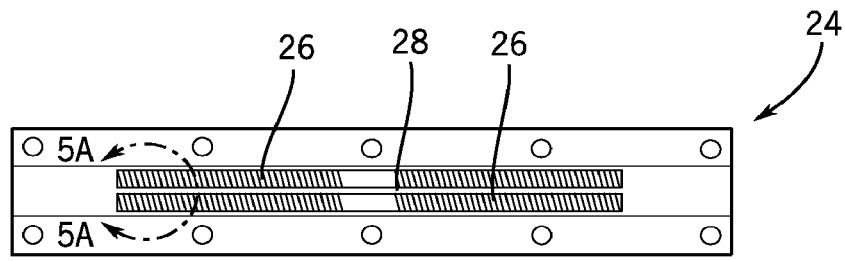
FIG. 5A is a top view of the anvil insert illustrated in FIG. 4A.
Figure 5B:
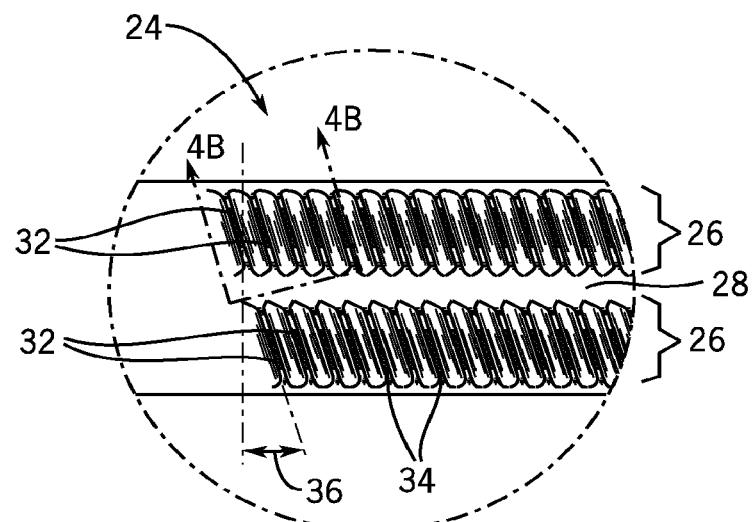
FIG. 5B is an enlarged view of FIG. 5A and showing a bond pattern.
Figure 5C:
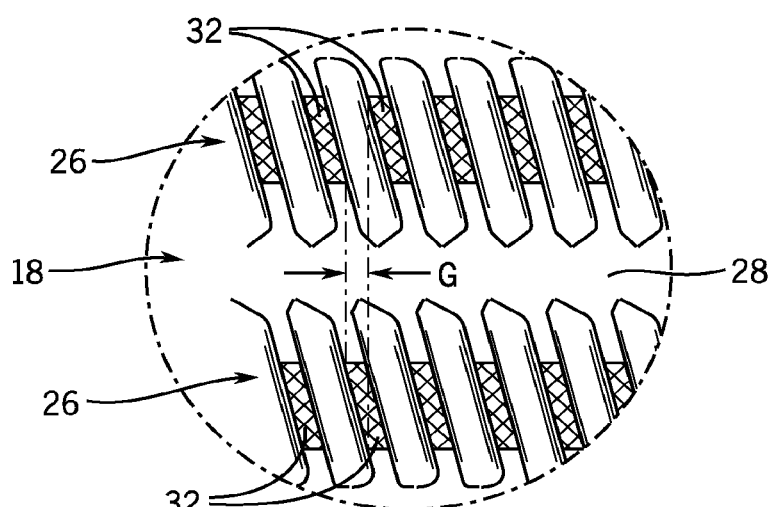
FIG. 5C is an enlarged view of FIG. 5B.

Referring now to FIGS. 4A, 4B, 5A, 5B, and 5C, further details of the anvils 14A, 14B are provided according to one embodiment. The anvils 14A, 14B may each be provided with an anvil insert 24 having a predetermined profile. The anvil insert 24 illustrated in these views includes a pair of spaced apart seal surfaces 26 having a recess 28 therebetween and wherein the seal surfaces 26 are provided with a series of canted rectangular patterns or teeth 32 thereon. The canted orientation of the rectangular pattern 32 provides both trailing edge and leading-edge coverage in a cross-machine direction. This arrangement allows even wear on the horns 16A, 16B interfacing with the anvils 14A, 14B such that the need to re-grind worn horns 16A, 16B is greatly reduced thereby also reducing downtime for horn 16A, 16B maintenance. With particular reference to FIGS. 5B and 5C, the canted arrangement of the rectangles or teeth 32 creates a bond pattern that will evenly wear a corresponding ultrasonic horn 16A, 16B. The edges 34 of adjacent teeth 32 are parallel to one another and are angled relative to the machine direction at a predetermined angle 36 (see FIG. 5B) that provides a following tooth 32 to fill in any gaps G (see FIG.

5C) existing between any preceding tooth 32. Depending on the geometry, such as width of gap between teeth 32 rows, width of gap between teeth 32, and the like, the predetermined angle 36 may provide full coverage of the ultrasonic horn 16A, 16B to achieve the goal of even wear. The anvil insert 24 of these views may be used to simultaneously bond adjacent article end portions 38 with cross-machine direction bonds 40, as shown in FIGS. 6A and 6B, while reserving a boundary between the sealed end portions for a later severing operation.

Figure 7:
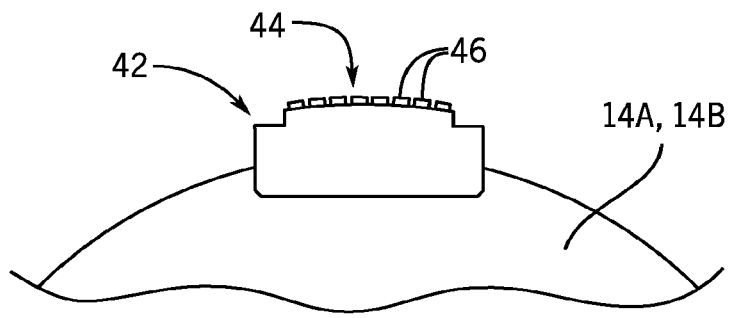
FIG. 7 is an enlarged view of an anvil insert for use with the anvils of the bonding system of FIG. 1, according to an embodiment of the invention.
Figure 8A:
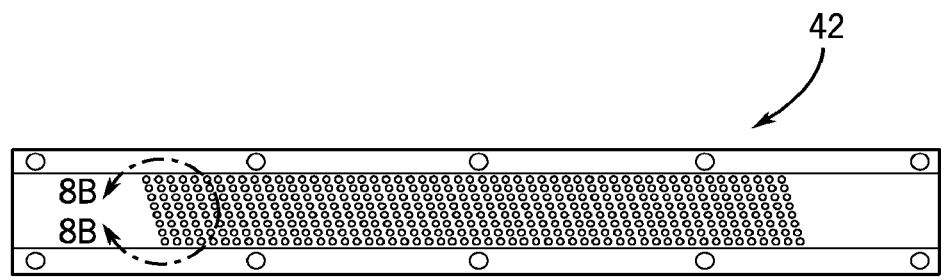
FIG. 8A is a top view of the anvil insert illustrated in FIG. 7.
Figure 8B:
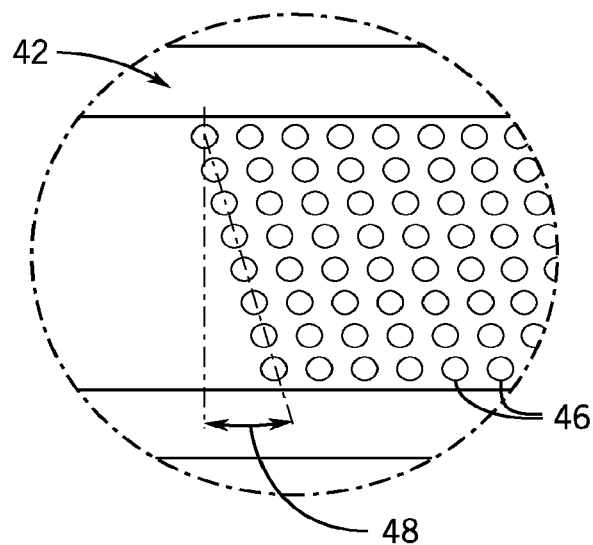
FIG. 8B is an enlarged view of FIG. 8A and showing a bond pattern.
Figure 9:
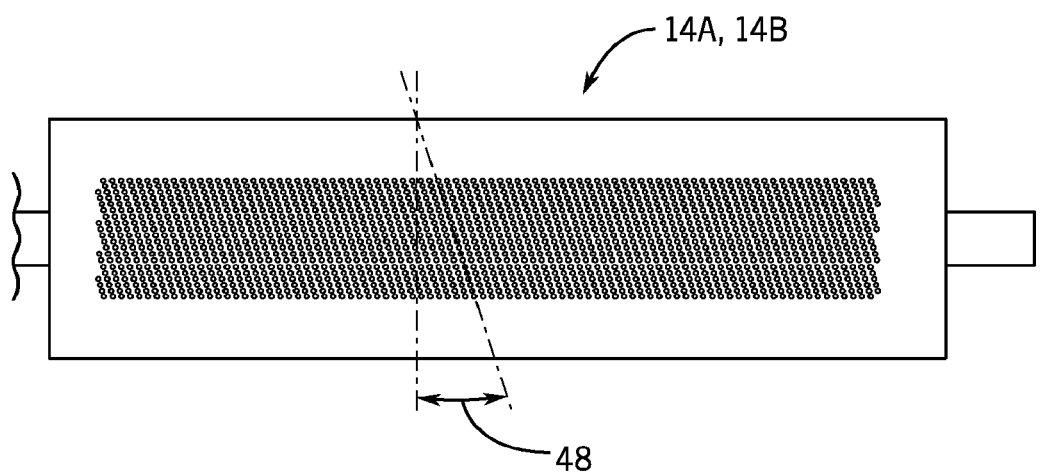
FIG. 9 is an enlarged view of an anvil for use in the bonding system of FIG. 1, according to an embodiment of the invention.

An alternative embodiment of an anvil insert A is illustrated in FIGS. 7, 8A, and 8B. The anvil insert 42 includes a seal surface 44 having a plurality of raised seal areas 46 arranged in a pattern that is canted from the machine direction at an angle 48. Alternatively, and as seen in FIG. 9, the pattern shown in FIGS. 8A and 8B may be applied to the entire surface of anvil 14A, 14B.

Figure 10:
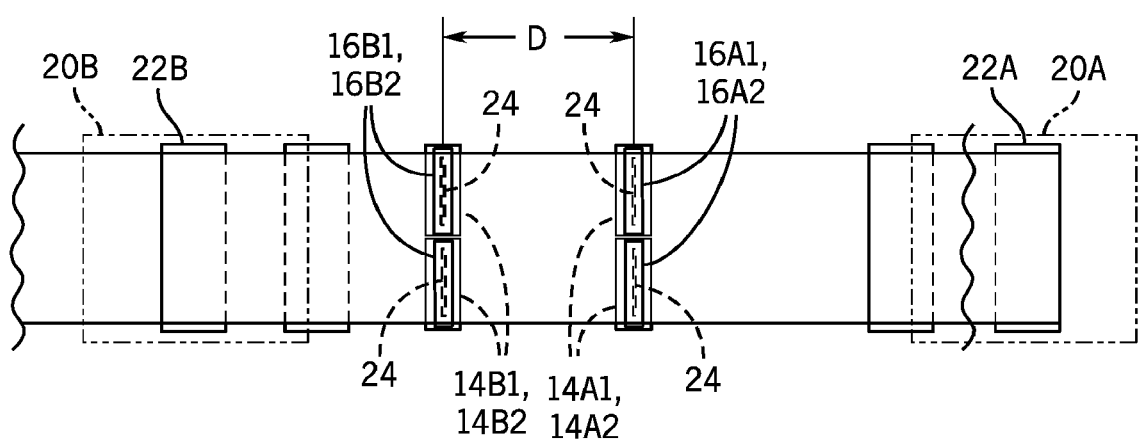
FIG. 10 is a top plan view showing an arrangement of paired anvils and ultrasonic horns for use in the bonding system of FIG. 1, according to an embodiment of the invention.

FIG. 10 illustrates an alternative arrangement of anvils and ultrasonic horns. In this embodiment, anvil pairs 14A1, 14A2 and 14B1, 14B2 are utilized rather that the single anvils 14A, 14B, illustrated in previous views. Ultrasonic horn pairs 16A1, 16A2 and 16B1, 16B2 correspond to and cooperate with the anvil pairs 14A1, 14A2 and 14B1, 14B2.

Figure 6A:
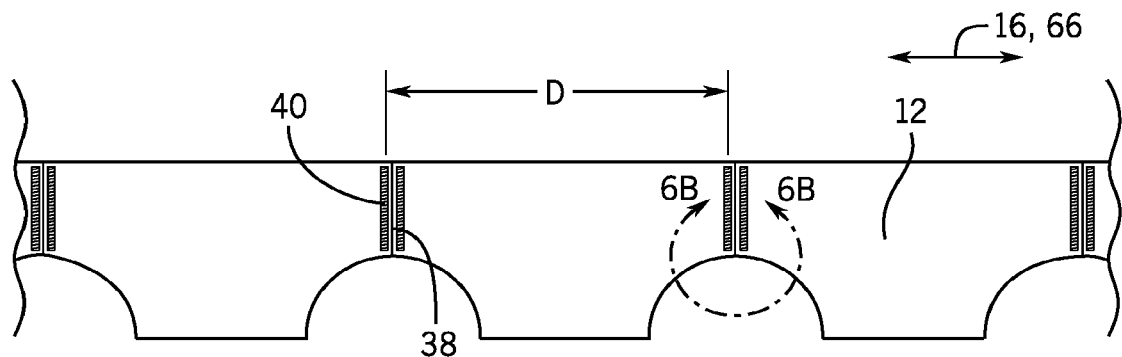
FIGS. 6A and 6B are top plan views of the web in FIG. 1 with spaced apart bonds.
Figure 6B:
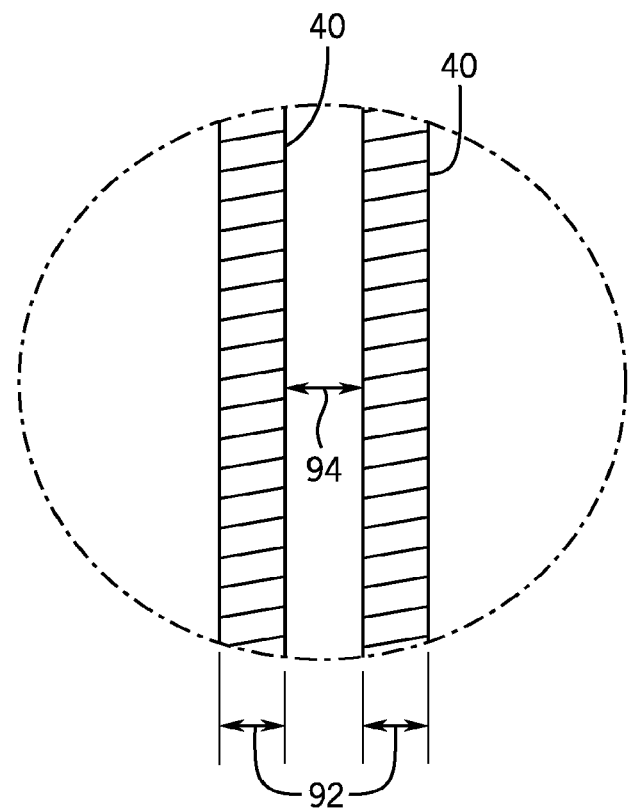

Referring again now to FIGS. 1 and 2, the predetermined distance d1 of the spacing of the first and second anvils 14A, 14B may be controlled to define the distance between the resulting bonds 40 on the web 12 (FIGS. 6A and 6B), with the resulting bonds 40 being located at what is to be an end portion 38 of an individual finished article (FIGS. 6A and 6B). The predetermined distance d1 may be changed to accommodate various sizes of the finished product, since the distance d1 corresponds to the length of the individual article. Accordingly, the length of the individual article may be changed by adjusting the position of the first or second ultrasonic horn 16A, 16B with respect to the other ultrasonic horn 16A, 16B.

As shown in FIGS. 1 and 2, the system 10 is configured to change the distance between a selected anvil 14A, 14B and horn 16A, 16B and the adjacent anvil 14A, 14B and horn 16A, 16B (e.g., from d1 to d2) via operation of a device for linear reciprocation of a selected anvil 14A, 14B and ultrasonic horn 16A, 16B relative another anvil 14A, 14B and ultrasonic horn 16A, 16B and to move in the direction of arrow B, (see FIG. 2), with drive devices 50, such as electric motors, pneumatic actuators, or hydraulic actuators for example, and associated linear actuators 52 providing such linear reciprocation in the embodiment of FIGS. 1 and 2. Preferably, the selected anvil 14A, 14B and ultrasonic horn 16A, 16B combination is slidingly mounted to a base structure 54 to provide for linear translation thereof. Since the distance d1, d2 intervals of bonding positions may be changed by changing the position of the first or second ultrasonic horn 16A, 16B, the present system may easily produce individual articles of various sizes. It is to be understood that while the view of FIG. 2 illustrates movement of the second ultrasonic horn 16B, the position of the first ultrasonic horn 16A may also or alternatively be changeable, as required by a specific application.

According to one embodiment, the distance d1, d2 between a selected anvil 14A, 14B and horn 16A, 16B and the adjacent anvil 14A, 14B and horn 16A, 16B may be controlled via a closed-loop control system 56. The control system 56 may operate one or more electric motors 50A, 50B for linearly translating a desired anvil and horn pair 14A, 14B, 16A, 16B along base structure 54, along with a vision system (e.g., camera) 58 that provides input to the control system 56 regarding positioning/spacing of the anvil and horn pairs 14A, 14B, 16A, 16B. In operation, the vision system 58 acquires images of bonding system 10—and specifically of the positioning of anvils 14A, 14B and horns 16A, 16B on base structure 54. The vision system 58 provides these images as an input to control system 56, which may include a processor 60 therein that analyzes the images to determine therefrom a spacing between the anvil and horn pairs 14A, 14B, 16A, 16B. The processor 60 then compares the spacing between the anvil and horn pairs 14A, 14B, 16A, 16B to a pre-determined desired spacing between the anvil and horn pairs (as set based on a size of the finished product and the spacing/location of bonds to be formed thereon). If the spacing between the anvil and horn pairs 14A, 14B, 16A, 16B, as measured from images acquired by vision system 58, is the same as the pre-determined desired spacing, then the positioning of the anvil and horn pairs 14A, 14B, 16A, 16B is left unchanged. Conversely, if the spacing between the anvil and horn pairs 14A, 14B, 16A, 16B is different from the pre-determined desired spacing, then the positioning of one or more of the anvil and horn pairs 14A, 14B, 16A, 16B is changed so as to adjust the spacing therebetween. In changing the positioning of one or more of the anvil and horn pairs 14A, 14B, 16A, 16B, the control system 56 causes one or more of the electric motors 50A, 50B to operate its associated linear actuator 52A, 52B to cause linear translation or sliding of anvil and horn pair(s) 14A, 14B, 16A, 16B along base structure 54. As positioning of one or more of the anvil and horn pairs 14A, 14B, 16A, 16B is changed, continuous feedback may be acquired from vision system 58 until it is determined that spacing between the anvil and horn pairs 14A, 14B, 16A, 16B matches the pre-determined desired spacing thereof—at which time activation of the electric motors 50A, 50B is terminated. According to embodiments of the invention, the above described closed-loop control system 56 provides for adjustment of the distance d1, d2 between the anvil and horn combinations 14A, 16A 14B, 16B at start-up of the system 10 and/or during operation of the system 10.

In another embodiment, rather than a closed-loop control, vision system 58 may operate to acquire images of the positioning of anvil and horn pairs 14A, 14B, 16A, 16B that are subsequently utilized by an operator to manually alter positioning thereof. That is, vision system 58 provides images to processor 60, which analyzes the images to determine spacing between the anvil and horn pairs 14A, 14B, 16A, 16B and then provides the determined spacing as an output to an operator, such as a displayed numerical output. The operator may then control spacing between the anvil and horn pairs 14A, 14B, 16A, 16B by manually controlling one or more of electric motors 50A, 50B to operate its associated linear actuator 52A, 52B to cause linear translation or sliding of anvil and horn pair(s) 14A, 14B, 16A, 16B along base structure. As one example, the operator may alter the positioning of one or more of the anvil horn pairs 14A, 14B, 16A, 16B via use of +/− buttons included on control system 56. In such a manner, the positioning of one or more of the anvil horn pairs 14A, 14B, 16A, 16B may be incrementally adjusted until it is determined by vision system 58/control system 56 that spacing between the anvil and horn pairs 14A, 14B, 16A, 16B matches the pre-determined desired spacing thereof.

Figure 11:
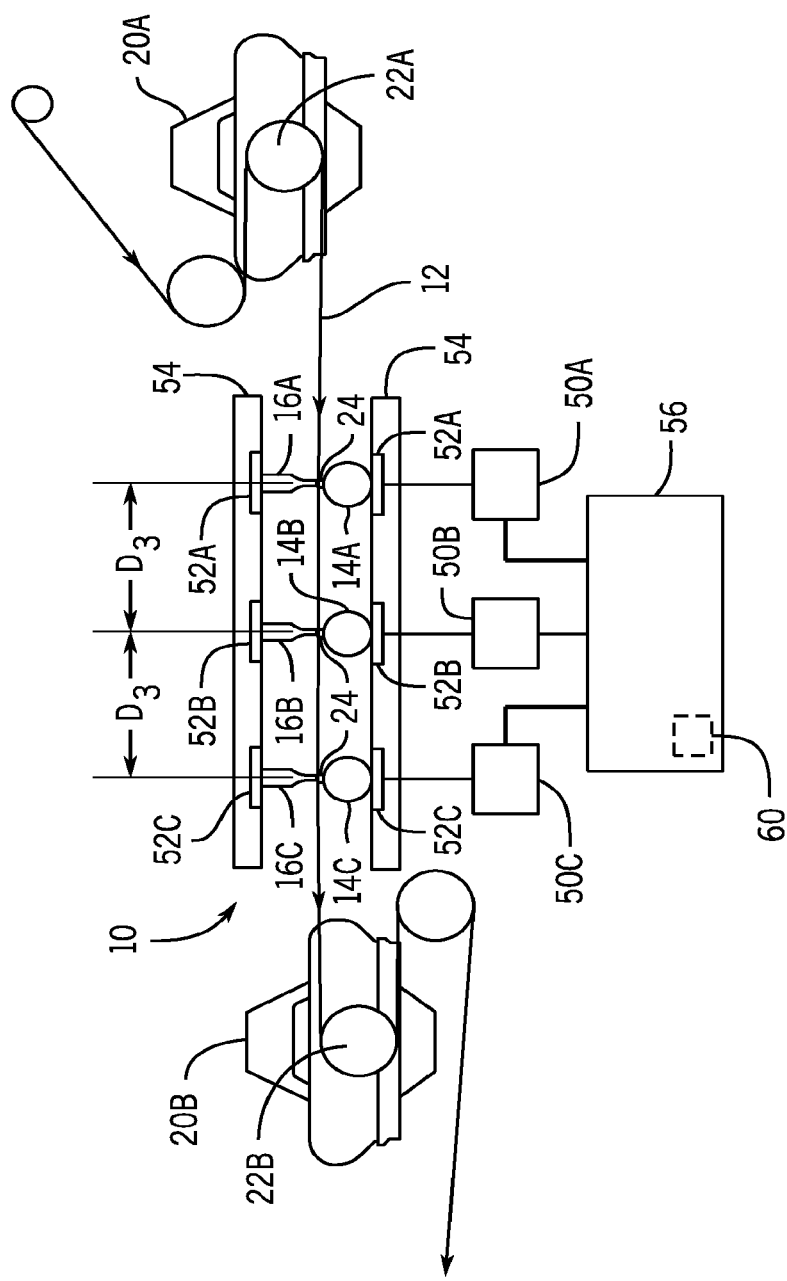
FIG. 11 is a schematic view of a bonding system including a plurality of anvil-horn combinations, according to an embodiment of the invention.
Figure 12:
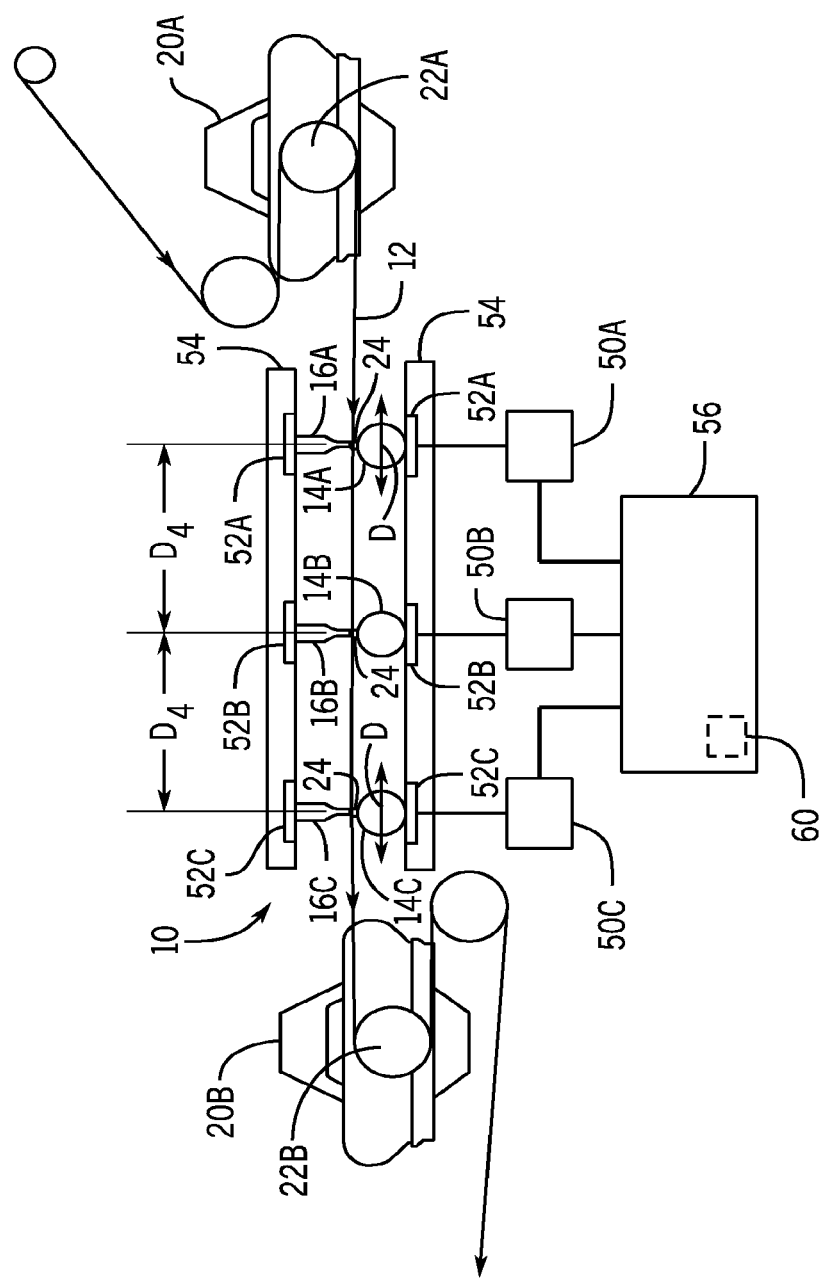
FIG. 12 is a schematic view of the bonding system of FIG. 11 with one or more of the anvil-horn combinations moved to vary a distance between the anvil-horn combinations.

Referring now to FIGS. 11 and 12, an alternative embodiment of bonding system 10 additionally includes a third anvil 14C, provided with an anvil insert 24 having a predetermined profile as described above, and a third ultrasonic horn 16C. The anvils 14A, 14B, 14C are laterally spaced apart inline and in a machine direction 16. As in the previous embodiment, the ultrasonic horns 16A, 16B, 16C apply vibration energy to the web 12 simultaneously and in cooperation with a respective anvil 14A, 14B, 14C to bond a respective portion of the web 12 that is to be an end portion 38 of an individual finished article 12 (FIGS. 6A and 6B). The anvils 14A, 14B, 14C with the corresponding horns 16A, 16B, 16C are spaced apart a predetermined distance d3 that corresponds to the distance between bonds 40 on the finished article 12 (see FIGS. 6A and 6B). Accordingly, the length of the individual article may be changed by adjusting the position of the first, second, or third ultrasonic horn 16A, 16B, 16C with respect to any other ultrasonic horn 16A, 16B, 16C. The bonding system 10 may include any combination of fixed and moveable ultrasonic horns 16A, 16B, 16C, such as, but not limited to: one fixed ultrasonic horn with two movable ultrasonic horns; two fixed ultrasonic horns and one movable ultrasonic horn; three fixed ultrasonic horns; and three movable ultrasonic horns, by way of non-limiting example.

With the possible combinations of fixed and moveable ultrasonic horns 16A, 16B, 16C, indicated above, one or more selected anvils 14A, 14B, 14C and ultrasonic horns 16A, 16B, 16C may thus be linearly reciprocated relative to other anvils 14A, 14B, 14C and ultrasonic horns 16A, 16B, 16C, as indicated by arrow D, to thereby change the distance from d3 to d4 (FIG. 12) between a selected anvil 14A, 14B, 14C and horn 16A, 16B, 16C and the adjacent anvil 14A, 14B, 14C and horn 16A, 16B, 16C. Such movement of the anvils 14A, 14B, 14C and ultrasonic horns 16A, 16B, 16C may be controlled via operation of electric motors 50 and associated linear actuators 52 by control system 56, in a similar manner as described above relative to FIGS. 1 and 2.

Figure 13:
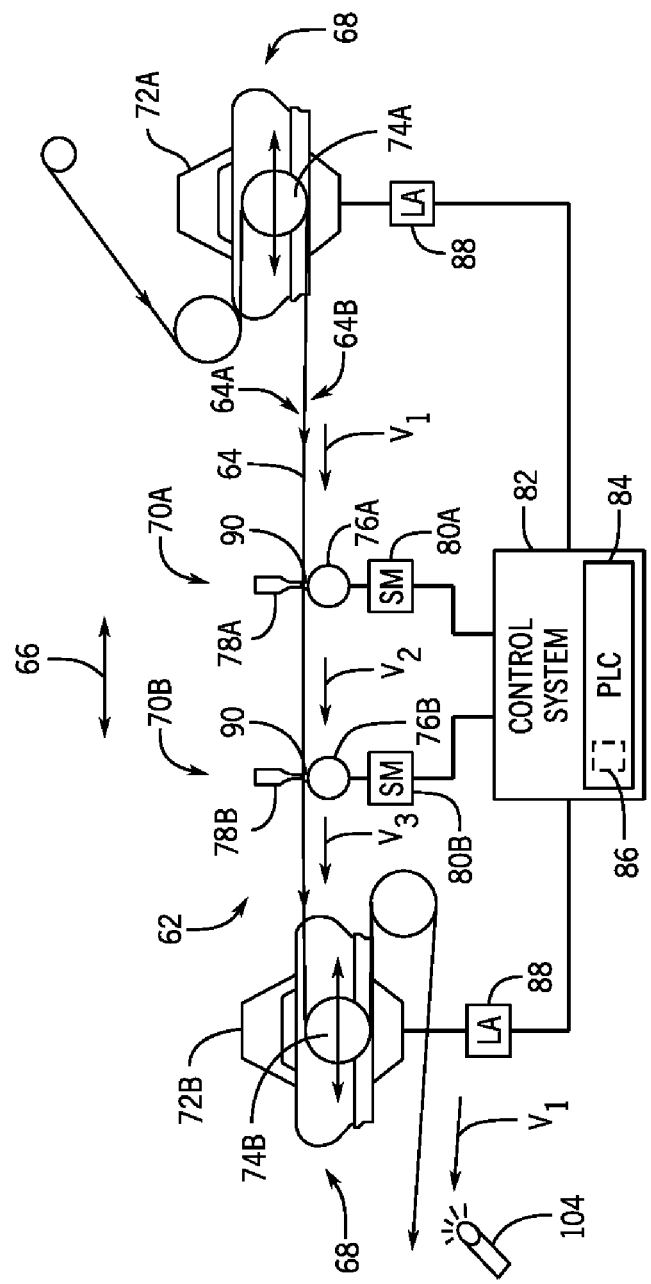
FIG. 13 is a schematic view of a bonding system operable to provide phasing between speed/movement of anvils and a web, according to an embodiment of the invention.

Referring now to FIG. 13, a bonding system 62 is illustrated according to another embodiment where movement of the anvil (e.g., rotational speed/velocity thereof) is selectively controlled to be brought into phase with a speed of the web, in order to control the anvil dwell time against the web. While the system 62 (and technique for operation thereof) is described below relative to an ultrasonic bonding system and ultrasonic bonding technique that utilize an anvil and ultrasonic horn combination, it is contemplated that the system/technique described below may be extended to any other known thermal or pressure bonding system that utilizes an anvil for bonding on a moving web. For example, a bonding system that forms pressure welds via interaction of a patterned anvil and a smooth roller (instead of an ultrasonic horn) and the use of active or passive thermal heating, is considered to be within the scope of the invention. Additionally, while the system 62 is described below with regard to controlling a bonding system that uses two bonding apparatuses (i.e., horn/anvil combinations), it is recognized that a system 62 could also be implemented having more than two bonding apparatuses or only a single bonding apparatus.

As shown in FIG. 13, a web of material 64—formed from a first web layer 64A and a second web layer 64B (as described hereafter) or from a unitary web structure that is folded—is fed in the machine direction 66. The layers of web 64 are materials capable of fusing to one another upon application of an applied energy that causes one or both of the layers 64A, 64B to soften or melt and join together without the use of an intermediate layer of adhesive material such as glue. The facing pair of web layers 64A, 64B may be the same type of material or different materials according to alternative embodiments. As non-limiting examples, first and second web layers 64A, 64B may include nonwoven materials, woven materials, films, foams, and/or composites or laminates of any of these material types.

Bonding system 62 includes a velocity changing feeding assembly 68 (or more generally "velocity changing device") that feeds the web 12 to one or more bonding apparatuses and controls a velocity thereof, with the one or more bonding apparatuses being, for example, two bonding apparatuses 70A, 70B shown in FIG. 13—although it is recognized that only a single bonding apparatus may be included in the system 62. The velocity changing device 68 comprise operates to increase and decrease the moving velocity of the web 64—with it being recognized that the velocity-changing device may comprise any of web festoon accumulators, a vertical accumulator series, or a horizontal accumulator series, for example, although web festoon accumulators are specifically illustrated in FIG. 13. According to the illustrated embodiment, velocity changing device 68 includes a first web festoon accumulator 72A having a first accumulator roller 74A, and a second web festoon accumulator 72B having a second accumulator roller 74B. The first web festoon accumulator 72A receives the web 64 flowing from an upstream side and releases the webs toward the bonding apparatuses 70A, 70B while the second web festoon accumulator 72B receives the web 64 from the bonding apparatuses 70A, 70B and moves the web 64 toward a downstream side. The velocity-changing device 68 further includes means (e.g., linear actuator 88) for moving the first and second accumulator rollers 74A, 74B in a unison, linear manner to thereby change the velocity of the web 64 that is received from an initial velocity V1 (i.e., a "feed velocity"). Specifically, the spacing between first and second accumulator rollers 74A, 74B may be adjusted to change the velocity to a second, slower velocity V2 for performing bonding of the web 64 (i.e., a "bonding velocity"), such that the dwell time of the web 64 during the bonding operation is adequate for proper bonding. The spacing between first and second accumulator rollers 74A, 74B may also be adjusted to change the velocity to a velocity V3 once the web 64 is bonded, before being transported by the second web festoon accumulator 72B again at the first V1 velocity.

The bonding apparatuses 70A, 70B of bonding system 62 may be any known ultrasonic welding systems in alternative embodiments, including, as non-limiting examples, a rotary ultrasonic welding system or a blade ultrasonic welding system. In the illustrated embodiment, bonding apparatuses 70A, 70B each include a rotary anvil 76A, 76B and an ultrasonic fixed blade horn 78A, 78B, also known as a sonotrode, which cooperate with each other to bond (i.e., fuse) the first web layer 64A to the second web layer 64B. Alternative embodiments may include multiple fixed blade horns or one or more rotary horns. A motor (not shown) that drives the ultrasonic horn 78A, 78B and a vibration control unit (not shown) that ultrasonically energizes the horn 78A, 78B and causes the horn to vibrate are also included in bonding apparatus, as well as an anvil actuator 80A, 80B operatively coupled to each anvil 76A, 76B to drive the anvil 76A, 76B. According to one embodiment, the anvil actuators 80A, 80B may be configured as servo motors (and are thus hereafter referred to as "servo motors 80A, 80B"), but it is recognized that the anvil actuators 80A, 80B may be any suitable device that effects actuation of the anvils 76A, 76B. The horn 78A, 78B and anvil 76A, 76B of each bonding apparatus 70A, 70B are positioned in a spaced relationship relative to one another to facilitate ultrasonically bonding the first and second web layers 64A, 64B to one another. During the bonding process, the web layers 64A, 64B are exposed to an ultrasonic emission from the horn 78A, 78B that increases the vibration of the particles in the web layers 64A, 64B. The ultrasonic emission or energy is concentrated at specific bond points where frictional heat fuses the web layers 64A, 64B together without the need for consumable adhesives.

According to an embodiment of the invention, a control system 82 is included in bonding system 62 that functions to control operation of the bonding apparatuses 70A, 70B and the velocity changing device 68. The control system 82 may comprise a programmable logic controller 84 operably connected to the bonding apparatuses 70A, 70B and the velocity changing device 68 via wired or wireless connections that provide for the communication of signals (inputs, control signals, etc.) therebetween. The programmable logic controller 84 includes one or more processors 86 for processing data acquired during operation of bonding systems 70A, 70B and/or for generating command signals that control operation of bonding apparatuses 70A, 70B and the velocity changing device 68.

The control system 82 is in operable communication with velocity changing device 68 in order to selectively control a velocity of the web 64 as it is provided to the bonding apparatuses 70A, 70B from the velocity changing device 68. In one embodiment, control system 82 is in operable communication with linear actuators 88 of the web festoon accumulators that position first and second accumulator rollers 74A, 74B, so as to selectively control operation of the linear actuators 88 and thereby control the velocity of the web 64. As previously described, first and second accumulator rollers 74A, 74B may be moved to thereby change the velocity of the web 64 from an initial velocity V1 to a second, slower velocity V2 during bonding of the web 64 and to a velocity V3 once the web 64 is bonded, before being transported by the second web festoon accumulator 72B again at the first V1 velocity.

The control system 82 is also in operable communication with bonding apparatuses 70A, 70B in order to selectively control the motors (not shown) that drive the ultrasonic horns 78A, 78B and the vibration control units (not shown) that ultrasonically energizes the horns 78A, 78B and causes the horns 78A, 78B to vibrate, as well as control servo motors 80A, 80B to drive the anvils 76A, 76B. With regard to controlling the servo motors 80A, 80B that drive anvils 76A, 76B, the control system 82 transmits control signals to servo motors 80A, 80B to control a movement of the anvils 76A, 76B, such as by setting a rotational speed or velocity of the rotary anvils 76A, 76B in the embodiment of FIG. 13. The velocity may be varied to thereby influence the dwell time of the anvils 76A, 76B (i.e., anvil insert 90, which may be configured as insert 24 shown in FIGS. 4A, 4B, 5A, 5B, 5C, for example) against the web 64. For example, the revolution speed of the anvils 14A, 14B is varied such that, the revolution speed of the anvils 14A, 14B from the upstream side may be slowed to second, slower velocity, such that the dwell time of the web 64 during the bonding operation is adequate for proper bonding. Once the web 64 is bonded, the anvils 14A, 14B accelerate to an increased velocity to be rotated back to the first velocity, and in a downstream direction.

According to an exemplary embodiment, control system 82 controls operation of the velocity changing device 68 and bonding apparatuses 70A, 70B such that the velocity/speed of the web 64 is phased with the velocity/speed of the anvils 76A, 76B. That is, control system 82 controls operation of the velocity changing device 68 and bonding apparatuses 70A, 70B such that increases in a velocity of the web 64 correspond to increases in a velocity of the anvils 76A, 76B, and likewise decreases in a velocity of the web 64 correspond to decreases in a velocity of the anvils 76A, 76B. By phasing the velocity/speed of the web 64 with the velocity/speed of the anvils 76A, 76B, the dwell time of the anvils 76A, 76B against the web 64 can be selectively controlled, such as the dwell time being maximized when desired. The controlling of the dwell time of the anvils 76A, 76B against the web 64 allows for bonds of a desired length (in the machine direction 66) to be formed on the web 64, with the length of the bonds being selectively controllable based on product type/size, web materials, and the strength of the bonds that is required. Referring back to FIGS. 6A and 6B, bonds 40 are shown therein in greater detail, with it being seen in the close-up view of FIG. 6B that bonds have a length 92 in the machine direction 66. As indicated above, the length 92 of each of the bonds 40 in the bond pattern may be selectively controlled based on the dwell time of the anvils 76A, 76B against the web 64, as determined at least in part by the velocity/speed of the web 64 and the velocity/speed of the anvils 76A, 76B. Additionally, by varying the length 92 of adjacent bonds 40, a spacing 94 between bonds 40 can also be selectively controlled. According to an embodiment, the length 92 of bonds 40 and/or spacing 94 between bonds 40 can be varied by as much as 25% by controlling the dwell time of the anvils 76A, 76B against the web 64.

Figure 14:
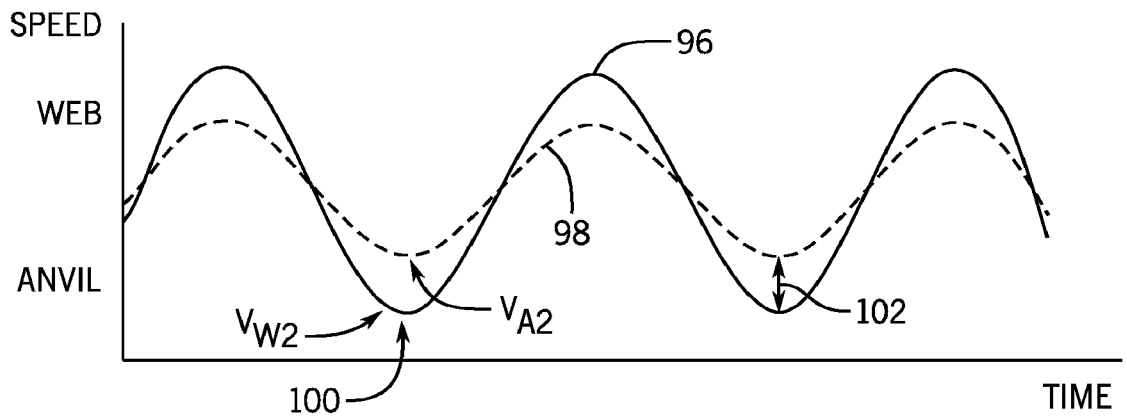
FIG. 14 illustrates velocity profiles of the web and anvils of the system of FIG. 13, where the speeds of the web and anvils are phased.
Figure 15:
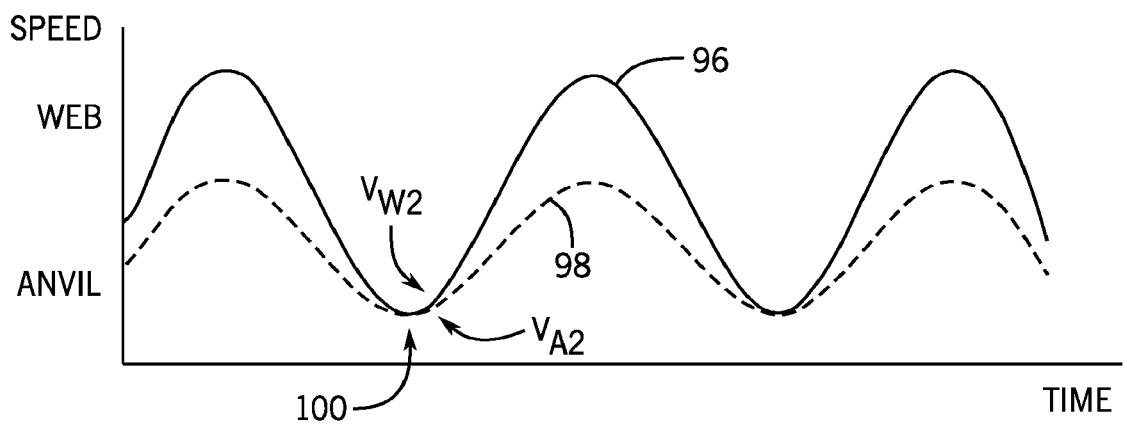
FIG. 15 illustrates velocity profiles of the web and anvils of the system of FIG. 13, where the speeds of the web and anvils are synchronized during a bonding period.
Figure 16:
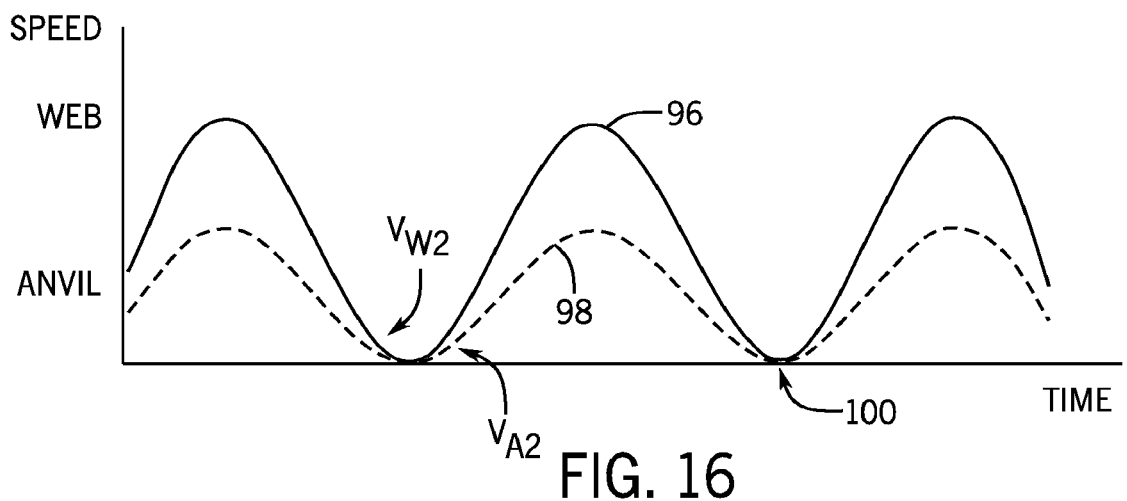
FIG. 16 illustrates velocity profiles of the web and anvils of the system of FIG. 13, where the speeds of the web and anvils are at zero speed during a bonding period.

FIGS. 14-16 illustrate velocity profiles of the web 64 and anvils 76A, 76B as controlled by control system 82, with the control system 82 controlling velocity changing device 68 and anvils 76A, 76B to synchronize the velocities of the web 64 and anvils 76A, 76B. According to an exemplary embodiment, the web velocity 96 and anvil (rotational) velocity 98 are controlled to have a sinusoidal profile, with the velocity of the web 64 and anvils 76A, 76B being brought to a bonding speed/velocity, indicated as web bonding velocity VW 2 and anvil bonding velocity VA 2, at a desired frequency. However, while the web velocity 96 and anvil velocity 98 profiles are depicted as sinusoidal in FIGS. 14-16, either or both of the velocity profiles could have a triangular, sawtooth, or other non-sinusoidal profile, according to alternative embodiments.

As illustrated in FIG. 14, in one embodiment, the web velocity 96 and anvil velocity 98 are synchronized with one another, but the velocity of the web 64 and the anvils 76A, 76B are not equal to each other during a bonding period 100 when bonds are formed on the web 64. That is, control system 82 controls velocity changing device 68 and servo motor 80A, 80B such that web 64 is translated at a bonding velocity VW 2 that is greater than an anvil bonding velocity VA 2 at which the anvils 76A, 76B rotate. The magnitude of the velocity mismatch between the web bonding velocity VW 2 and the anvil bonding velocity VA 2, indicated at 102, determines (in part) a length of the bonds formed on the web 64, as it impacts a dwell time of the web on the anvil, and this magnitude of the velocity mismatch 102 can be selectively controlled by an operator to thereby control the bond length.

Referring now to FIG. 15, velocity profiles of the web 64 and anvils 76A, 76B are shown according an embodiment where the speeds/velocities of the web 64 and anvils 76A, 76B are synchronized during a bonding period 100 when bonds are formed on the web 64 such that they are made equal or substantially equal (e.g., +/−5%) in magnitude during the bonding period 100. Stated another way, the velocity mismatch between the web velocity and the anvil velocity is brought to zero or substantially zero. Such synchronizing of the web velocity 96 and anvil velocity 98 at equal speeds enable the formation of "full" bonds on the web 64 having desirable bond strength.

In one specific embodiment of synchronizing the web and anvil speeds/velocities 86, 96 via control system 82, both the web velocity 96 and the anvil velocity 98 may be reduced to zero during a bonding period 100 when bonds are formed on the web 64 (i.e., "zero-speed bonding"), as shown in FIG. 16. The term zero-speed bonding as used herein refers to an embodiment where the web velocity 96 and the anvil velocity 98 are reduced to zero (i.e., not moving) during bonding of the web 64 or are reduced essentially to zero during bonding of the web 64—such as at a velocity of 0-200 m/min. Beneficially, the implementing of zero-speed bonding in bonding system 62 provides for the formation of straight bond lines on the web 64, which may be desirable from both a strength standpoint and an aesthetic standpoint.

Referring back now to FIG. 13, according to one embodiment, bonding system further comprises a vision system or systems 104 operatively coupled to control system 82 to provide feedback thereto regarding the bonds formed on web 64. The vision systems 104 may comprise high-speed cameras or other image capturing devices that are configured to acquire images of the bonds formed by bonding apparatuses 70A, 70B. A vision system 104 may be provided for each bonding apparatus 22 to acquire such bond images. The vision systems 104 provide the acquired image(s) to a processor 86 of control system 82, which analyzes the image(s) in order to determine a length of the bonds in the machine direction. The determined length of the bonds may be used for a number of different control purposes, including determining that the bonds being formed by bonding apparatuses 70A, 70B are of a desired length and/or when making an adjustment from an existing bond length to a new bond length and identifying when the bond length has been achieved.

According to one embodiment, the control system 82 operates as a closed-loop system utilizing the acquired image(s) as an input in order to selectively control operation of the servo motors 80A, 80B, for purposes of adjusting the rotational speed/velocity of the anvils 76A, 76B and thereby controlling a length of the bonds. The closed-loop control technique implemented by control system 82 allows for on-the-fly adjustments of bonding system 62 during operation thereof, whether it be to correct an identified error in the bonding and/or adjust the bond length to a desired value responsive to a changing of materials or a change of product size. Such adjustments can be made without having to change tooling in bonding system 62, but instead can be achieved via controlling of the anvil rotational speed/velocity in order to artificially change the bond length on web 64.

Figure 17:
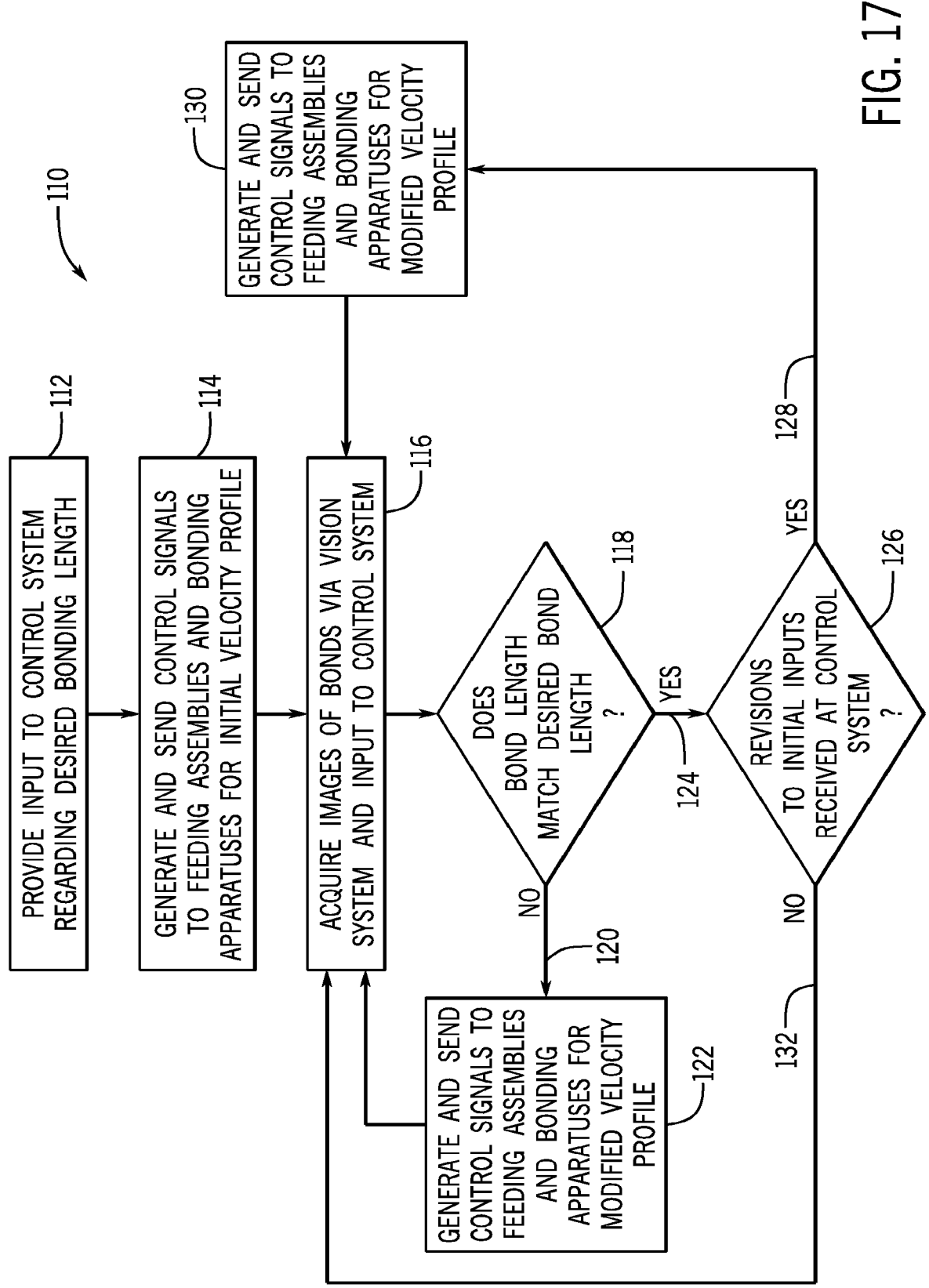
FIG. 17 is a flowchart illustrating a closed-loop control technique implemented for operating the system of FIG. 13 to control movement/speed of the web and anvils, according to an embodiment of the invention.

Referring now to FIG. 17, a flowchart illustrating a closed-loop control technique 110 implemented by control system 82 for controlling movement/speed of the web 64 and anvils 76A, 76B is provided, according to an embodiment of the invention. While the technique 110 is described below with regard to controlling a bonding system 62 that uses multiple bonding apparatuses 70A, 70B (i.e., horn/anvil combinations), it is recognized that the technique could also be used to control a system that utilizes only a single bonding apparatus. As shown in FIG. 17, technique 110 begins at STEP 112 with an input being provided to control system 82 regarding a pre-determined bond length (in the machine direction) to be formed on web 64 for bonding together layers 64A, 64B of the web. The input may be provided to control system 82 via an operator input, for example, and may be based on the size of the absorbent articles being fabricated and/or the material composition and thickness of the web material. Upon input of the pre-determined bond length, control system 82 operates to generate and send command signals to velocity changing device 68 and bonding apparatuses 70A, 70B (i.e., to servo motors 80A, 80B) in order to cause web 64 and anvils 76A, 76B to move according to an initial velocity profile, as indicated at STEP 114. As previously described, the web velocity 96 and anvil (rotational) velocity 98 may be controlled to have a sinusoidal profile, with the velocity of the web 64 and anvils 76A, 76B being phased with one another and having varying speeds/velocities during bonding and non-bonding periods. In one embodiment, the web velocity 96 and anvil velocity 98 are in-phase with one another but unequal during a bonding period when bonds are formed on the web 64, while in another embodiment the web velocity 96 and anvil velocity 98 are synchronized with one another (i.e., equal) during the bonding period.

Upon bonding system 62 beginning to operate under initial settings implemented by control system 82, the technique continues at STEP 116 with vision systems 104 acquiring images of bonds formed by bonding apparatuses 70A, 70B and subsequently providing said images to the control system 82 as input/feedback. A processor 86 of control system 82 analyzes the images in order to determine a length of the bonds in the machine direction and, at STEP 118, determines whether the bond length matches the length set by the operator. If it is determined that the bond length does not match the bond length set by the operator, as indicated at 120, then technique continues at STEP 122 with control system 82 sending modified control signals to the servo motors 80A, 80B that drive anvils 76A, 76B, so as to vary the movement/rotational velocity thereof. The modified control signals cause an adjustment of the movement/rotational velocity of the anvils 76A, 76B, at least during a bonding period of the web 64, such that a velocity mismatch between the web 64 and the anvils 76A, 76B is also modified. The altering of the velocity mismatch causes a corresponding change in the length of the bonds formed on web 64. Upon completion of STEP 122, the technique 110 then loops back to STEPS 116 and 118 with the vision systems 104 acquiring and transmitting images of bonds to the control system 82 as input/feedback, and the control system 82 determining whether the bond length matches the length set by the operator.

If it is determined at STEP 118 that the bond length matches the bond length set by the operator, as indicated at 124, then technique continues at STEP 126 with the control system 82 monitoring/determining whether any revisions to the initial inputs have been received. The revised inputs may be in the form of input provided to control system 82 via an operator input, for example, and may be based on a change in a size/type of product to be processed on bonding system 62, a change in web materials, and/or a change in the desired bond length/strength to be formed on web 64. The revised inputs are deemed to necessitate a change in the bond length formed by bonding apparatus(es).

If it is determined at STEP 126 that a revised input has been provided to control system 82, as indicated at 128, then technique continues at STEP 130 with control system 82 sending modified control signals to the servo motors 80A, 80B that drive anvils 76A, 76B (and optionally to velocity changing device 68) so as to vary the movement/rotational velocity thereof in accordance with the revised inputs. The modified control signals cause an adjustment of the movement/rotational velocity of the anvils 76A, 76B (and web 64), at least during a bonding period of the web 64, such that a velocity mismatch between the web 64 and the anvils 76A, 76B is also modified. The altering of the velocity mismatch causes a corresponding change in the length of the bonds formed on web 64. Upon completion of STEP 130, the technique then loops back to STEPS 116 and 118 with the vision systems 104 acquiring and transmitting images of bonds to the control system 82 as input/feedback, and the control system 82 determining whether the bond length matches the pre-determined length set by the operator.

If it is determined at STEP 126 that no revised input has been provided to control system 82, as indicated at 132, then technique loops back to STEPS 116 and 118 with the vision systems 104 acquiring and transmitting images of the bonds to the control system 82 as input/feedback, and the control system 82 determining whether the bond length matches the bond length set by the operator. That is, the control system 82 monitors operation of the bonding system to confirm that the bonds being formed on web 64 continue to match the bonds desired in the initial input settings provided to control system 82.

Figure 18:
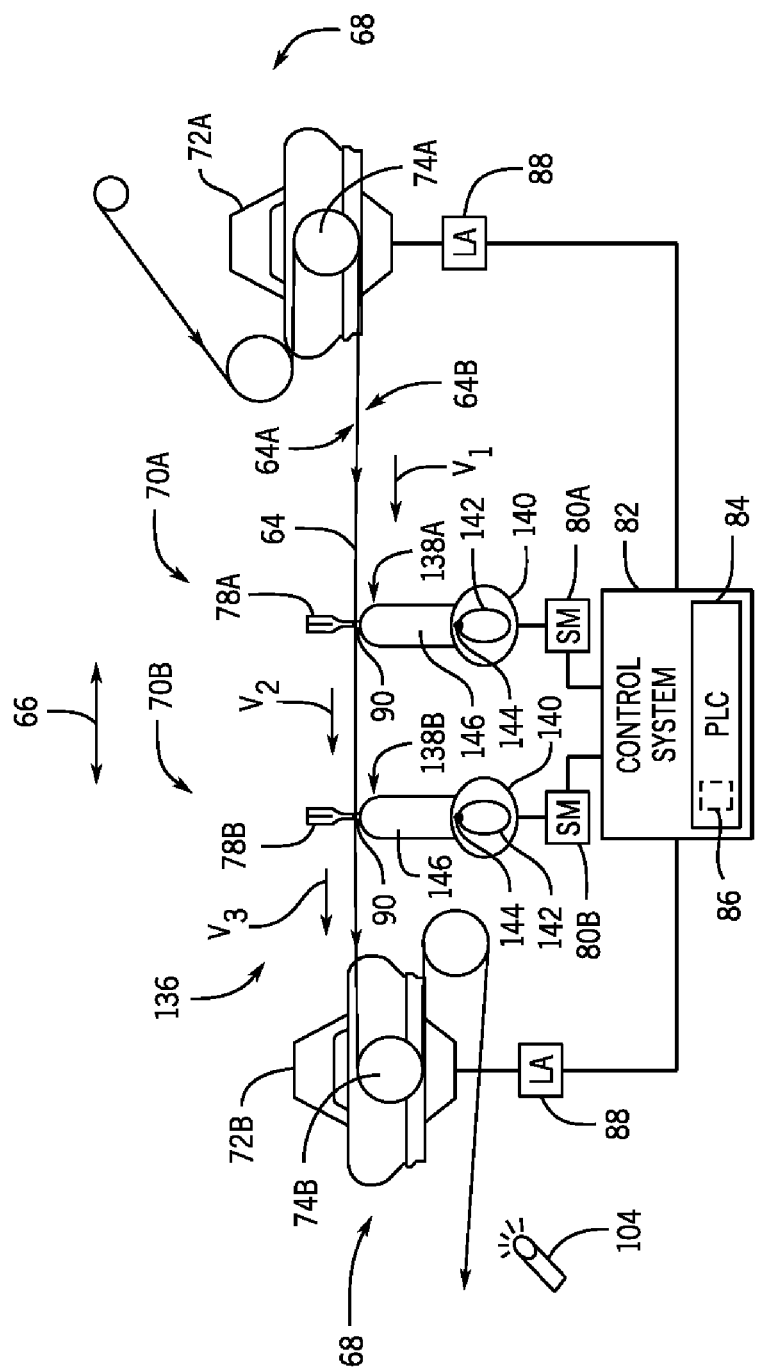
FIG. 18 is a schematic view of a bonding system operable to provide phasing between speed/movement of anvils and a web, according to an embodiment of the invention.

Referring now to FIG. 18, a bonding system 136 is illustrated according to another embodiment that includes one or more cammed or "wobble" anvils that follow a predetermined cyclical velocity profile. The cammed anvils 138A, 138B may be used in bonding system 136 instead of rotary anvils 76A, 76B as depicted in FIG. 13, with the cammed anvils 138A, 138B beneficially providing for a faster cycling time and/or enabling low speed operation of the bonding system 136 (i.e., low web speed and anvil movement/speed). Each cammed anvil 138A, 138B includes a cam wheel 140 having a cam track or surface 142 formed therein, a cam member 144 that translates within/around the cam track 142 when the cam wheel is rotated, and an anvil body 146 attached to the cam member 144 so as to translate therewith—with the anvil body 146 presenting a surface that interacts with horn 78A, 78B to enable the formation of ultrasonic bonds on web 64. The cam track 142 may comprise an irregular or oblong track in which the cam member 144 rides. As the cam member 144 rides along cam track 142, the anvil body 146 is caused to move therewith, with movement of the anvil body 146 comprising both vertical (up/down) movement and horizontal movement. The horizontal movement is in the machine direction when the anvil body 146 is proximate the horn 78A, 78B to form bonds on the web 64 via interaction of the anvil body and horn, as some horizontal movement of the anvil body 146 in the machine direction 66 is necessary when forming bonds with a web 64 moving at a web velocity in the machine direction. In an alternative embodiment, where zero-speed bonding is to be performed, it is recognized that the anvil body 146 may exhibit only vertical movement, as horizontal movement/rotation of the anvil body 146 would not be necessary in such an embodiment.

In operation of bonding system 136, a servo motor 80A, 80B operably connected to the cammed anvil 138A, 138B causes wheel 140 to rotate, thereby causing the cam member 144 to ride in the cam track 142 and cause cyclical displacement of the anvil body 146 relative to the horn 78A, 78B at a desired frequency and speed. In operation of bonding apparatuses 70A, 70B, control system 82 controls operation of servo motors 80A, 80B to phase the movement/rotational velocity of cammed anvils 138A, 138B with the movement/velocity of the web 64. The velocity profiles of the web 64 and anvils 138A, 138B may be controlled by control system 82 to match any of the profiles shown in FIGS. 14-16, for example, and may thus be controlled as phased movements/velocities, as synchronized movements/velocities, or according to a zero-speed bonding control.

Beneficially, embodiments of the invention thus provide an apparatus and method for controlling the speed of both a continuous web and a bonding apparatus in order to effectuate stronger bonds in the web, including phasing and/or synchronization of these speeds at a desired bonding time. An anvil in each of one or more anvil/horn combinations is selectively driven by a servo motor such that the movement/velocity thereof is phased with the movement/velocity of the web that is being bonded. By phasing the velocity/speed of the web with the velocity/speed of the anvil(s) in the bonding system, the dwell time of the anvil(s) against the web can be selectively controlled, such as the dwell time being maximized when desired. The controlling of the dwell time of the anvil(s) against the web allows for bonds of a desired length (in the machine direction) to be formed on the web, with the length of the bonds being selectively controllable based on product type/size, web materials, and the strength of the bonds that is required.

Embodiments of the invention also beneficially provide a system for selectively controlling the distance between a selected anvil and horn and the adjacent anvil and horn. A vision system may acquire data on the distance between adjacent anvil-horn combinations, with the data used in a closed-loop control system where a control system causes a motor and associated linear actuator to selectively adjust a position of one or more anvil-horn combinations or the data being provided to an operator to enable the operator to actively control a motor and associated linear actuator to selectively adjust a position of one or more anvil-horn combinations.

Therefore, according to one embodiment of the invention, a system for bonding a web comprising at least a pair of web layers includes a velocity changing device for increasing and decreasing a velocity of the web in a machine direction, an anvil and a corresponding ultrasonic horn that interact to form ultrasonic bonds on the web, and an anvil actuator configured to control a movement of the anvil. A control system is also included in the bonding system for controlling operation of the anvil actuator the velocity changing device, with the control system programmed to decrease a moving velocity of the web from a feed velocity to a bonding velocity as the web passes between the anvil and the ultrasonic horn and control movement of the anvil to synchronize the movement of the anvil with the moving velocity of the web.

According to another embodiment of the invention, a method for bonding a web having at least a pair of web layers includes moving a web in a machine direction via a feeding assembly, the feeding assembly configured to selectively control a velocity of the web. The method also includes feeding the web to one or more bonding apparatuses, each of the one or more bonding apparatuses comprising an anvil, an ultrasonic horn that interacts with the anvil to form ultrasonic bonds on the web, and an anvil actuator configured to control a velocity of the anvil. The method further includes controlling operation of the anvil actuator and the feeding assembly to synchronize the velocity of the web with a velocity of the anvil by decreasing the velocity of the web and the velocity of the anvil to a web bonding velocity and an anvil bonding velocity as the web passes between the anvil and the ultrasonic horn.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A bonding system for bonding a web comprising at least a pair of web layers, the bonding system comprising:
   a first bonding unit configured to form bonds on the web;
   a second bonding unit spaced apart from the first bonding unit in a machine direction and configured to form bonds on the web;
   a base structure comprising one or more sections, with the first bonding unit and the second bonding unit coupled to the base structure, and with one or both of the first bonding unit and the second bonding unit being translatable along the base structure in the machine direction or opposite the machine direction;
   an actuating structure configured to translate one or both of the first bonding unit and the second bonding unit along the base structure;
   a vision system configured to acquire positional data of the first bonding unit and the second bonding unit while the first and second bonding units are forming bonds; and
   a control system operably connected to the actuating structure and to the vision system, the control system including a processor configured to:
   receive the positional data from the vision system;
   analyze the positional data to determine a current spacing between the first bonding unit and the second bonding unit;
   compare the current spacing between the first bonding unit and the second bonding unit to a target spacing; and
   when the current spacing does not match the target spacing:
   automatically cause the actuating structure to translate one or both of the first bonding unit and the second bonding unit while the first and second bonding units are forming bonds along the base structure until a spacing between the first bonding unit and the second bonding unit matches the target spacing; or
   generate an operator output in operation indicating that the current spacing does not match the target spacing.

2. The bonding system of claim 1, wherein the vision system comprises a camera system configured to acquire images of the first bonding unit and the second bonding unit, the images providing the positional data on the first bonding unit and the second bonding unit regarding positions thereof along the base structure.

3. The bonding system of claim 1, wherein the control system comprises a closed-loop control system, with the processor configured to automatically cause the actuating structure to translate one or both of the first bonding unit and the second bonding unit along the base structure responsive to receipt and analysis of the positional data.

4. The bonding system of claim 3, wherein the processor is configured to:
   continuously receive the positional data on the first bonding unit and the second bonding unit as positioning of one or both of the first bonding unit and the second bonding unit is changed; and
   cause the actuating structure to stop translation of one or both of the first bonding unit and the second bonding unit upon the current spacing matching the target spacing.

5. The bonding system of claim 3, wherein the processor is configured to provide for adjustment of the spacing between the first bonding unit and the second bonding unit at start-up of the bonding system or responsive to a size change and associated change in machine direction bond spacing in the bonding system.

6. The bonding system of claim 1, wherein the actuating structure comprises:
   a first drive device and a first linear actuator operatively connected
   to the first bonding unit, the first drive device operating the first linear actuator to translate the first bonding unit along the base structure; and
   a second drive device and a second linear actuator operatively connected to the second bonding unit, the second drive device operating the second linear actuator to translate the second bonding unit along the base structure.

7. The bonding system of claim 1, wherein the operator output comprises a numerical display on the control system indicating the current spacing between the first bonding unit and the second bonding unit.

8. The bonding system of claim 7, wherein the control system comprises control buttons thereon actuatable by an operator to manually control the actuating structure to translate one or both of the first bonding unit and the second bonding unit along the base structure in the machine direction or opposite the machine direction.

9. The bonding system of 28, wherein the control buttons comprise:
   a first control button actuatable to cause the first bonding unit or the second bonding unit to translate along the base structure in the machine direction; and
   a second control button actuatable to cause the first bonding unit or the second bonding unit to translate along the base structure opposite the machine direction.

10. The bonding system of claim 1, wherein the target spacing corresponds to a pre-determined spacing between bonds to be formed on the web by the first bonding unit and bonds to be formed on the web by the second bonding unit.

11. The bonding system of claim 1, wherein each of the first bonding unit and the second bonding unit comprise an anvil and a corresponding ultrasonic horn that interact to form ultrasonic bonds on the web.

12. The bonding system of claim 1, further comprising a third bonding unit spaced apart from the first and second bonding units in the machine direction and configured to form bonds on the web;
   wherein the actuating structure is configured to translate one, two, or all of the first bonding unit, the second bonding unit, and the third bonding unit along the base structure;
   wherein the vision system is configured to acquire positional data on the third bonding unit; and
   wherein the processor is configured to:
   receive the positional data from the vision system;
   analyze the positional data to determine a current spacing between the first bonding unit, the second bonding unit, and the third bonding unit;
   compare the current spacing between the first bonding unit, the second bonding unit, and the third bonding unit to a target spacing; and when the current spacing does not match the target spacing:
    automatically cause the actuating structure to translate one, two, or all of the first bonding unit, the second bonding unit, and the third bonding unit along the base structure until a spacing between the first bonding unit, the second bonding unit, and the third bonding unit matches the target spacing; or
    generate an operator output indicating that the current spacing does not match the target spacing.

13. A method for controlling positioning of a first bonding unit and a second bonding unit in a bonding system for bonding a web comprising at least a pair of web layers, the method comprising:
    acquiring while the first and second bonding units are forming bonds, via a vision system associated with the bonding system, positional data on the first bonding unit and the second bonding unit regarding positioning thereof on a base structure that extends along a machine direction;
    analyzing, via a processor of a control system associated with the bonding system, the positional data to determine a current spacing between the first bonding unit and the second bonding unit along the base structure;
    comparing, via the processor, the current spacing between the first bonding unit and the second bonding unit to a target spacing; and
    when the current spacing does not match the target spacing, controlling while the first and second bonding units are forming bonds, via the processor, an actuating structure operably connected to one or both of the first bonding unit and the second bonding unit, the actuating structure being controlled to translate one or both of the first bonding unit and the second bonding unit along the base structure until a spacing between the first bonding unit and the second bonding unit matches the target spacing.

14. The method of claim 13, wherein acquiring positional data on the first bonding unit and the second bonding unit comprises acquiring visual images of the first bonding unit and the second bonding unit via the vision system.

15. The method of claim 13, wherein controlling the actuating structure comprises controlling the actuating structure according to a closed-loop control scheme, with the processor automatically causing the actuating structure to translate one or both of the first bonding unit and the second bonding unit along the base structure responsive to acquisition and analysis of the positional data.

16. The method of claim 13, wherein controlling the actuating structure comprises:
    controlling a first drive device and a first linear actuator operatively connected to the first bonding unit, the first drive device operable to cause the first linear actuator to translate the first bonding unit along the base structure; and
    controlling a second drive device and a second linear actuator operatively connected to the second bonding unit, the second drive device operable to cause the second linear actuator to translate the second bonding unit along the base structure.

17. A method for controlling positioning of a first bonding unit and a second bonding unit in a bonding system for bonding a web comprising at least a pair of web layers, the method comprising:
    acquiring while the first and second bonding units are forming bonds, via a vision system associated with the bonding system, positional data on the first bonding unit and the second bonding unit regarding positioning thereof on a base structure that extends along a machine direction;
    analyzing, via a processor of a control system associated with the bonding system, the positional data to determine a current spacing between the first bonding unit and the second bonding unit along the base structure;
    comparing, via the processor, the current spacing between the first bonding unit and the second bonding unit to a target spacing; and
    when the current spacing does not match the target spacing, generating while the first and second bonding units are forming bonds, via the processor, an operator output indicating that the current spacing does not match the target spacing.

18. The method of claim 17, wherein generating the operator output comprises generating a numerical display on a display of the control system indicating the current spacing between the first bonding unit and the second bonding unit.

19. The method of claim 17, further comprising:
    operably connecting an actuating structure to one or both of the first bonding unit and the second bonding unit that provides for translation of one or both of the first bonding unit and the second bonding unit along the base structure; and
    enabling control of the actuating structure via control buttons on the control system, the control buttons actuatable by an operator to manually control the actuating structure to translate one or both of the first bonding unit and the second bonding unit along the base structure in the machine direction or opposite the machine direction.

20. The method of claim 17, wherein acquiring positional data on the first bonding unit and the second bonding unit comprises acquiring visual images of the first bonding unit and the second bonding unit via the vision system.

\* \* \* \* \*